(12) United States Patent
Quintessenza

(10) Patent No.: US 7,862,610 B2
(45) Date of Patent: *Jan. 4, 2011

(54) BICUSPID VASCULAR VALVE AND METHODS FOR MAKING AND IMPLANTING SAME

(76) Inventor: James Quintessenza, 6101-54 St. South, St. Petersburg, FL (US) 33715

( * ) Notice: Subject to any disclaimer, the term of this patent is extended or adjusted under 35 U.S.C. 154(b) by 402 days.

This patent is subject to a terminal disclaimer.

(21) Appl. No.: 11/939,452

(22) Filed: Nov. 13, 2007

(65) Prior Publication Data

US 2008/0065198 A1    Mar. 13, 2008

Related U.S. Application Data

(63) Continuation-in-part of application No. 11/041,603, filed on Jan. 24, 2005, now Pat. No. 7,320,705.

(60) Provisional application No. 60/538,870, filed on Jan. 23, 2004.

(51) Int. Cl.
*A61F 2/06* (2006.01)
(52) U.S. Cl. ...................................... 623/2.12
(58) Field of Classification Search .......... 623/2.1–2.24
See application file for complete search history.

(56) References Cited

U.S. PATENT DOCUMENTS

| | | | |
|---|---|---|---|
| 2,922,437 A | 1/1960 | Rippingilla | |
| 4,340,977 A | 7/1982 | Brownlee et al. | |
| 4,790,844 A | 12/1988 | Ovil | |
| 5,344,442 A | 9/1994 | Deac | |
| 5,500,015 A * | 3/1996 | Deac | 606/167 |
| 5,824,063 A | 10/1998 | Cox | |
| 6,299,637 B1 | 10/2001 | Shaolian et al. | |
| 6,517,576 B2 | 2/2003 | Gabbay | |
| 6,673,109 B2 | 1/2004 | Cox | |
| 6,682,559 B2 | 1/2004 | Myers et al. | |
| 6,752,828 B2 | 6/2004 | Thornton | |
| 6,875,230 B1 | 4/2005 | Morita et al. | |
| 7,163,556 B2 | 1/2007 | Xie et al. | |

(Continued)

OTHER PUBLICATIONS

International Search Report for PCT/US2008/083426, mailed Mar. 6, 2009, 7 pgs.

(Continued)

*Primary Examiner*—Suzette J Gherbi
(74) *Attorney, Agent, or Firm*—Squire, Sanders & Dempsey, L.L.P.

(57) ABSTRACT

A vascular valve constructed from a biocompatible material that is designed to be surgically implanted in a patient's blood vessel, such as the right ventricular outflow tract. At the first end of the valve there is an orifice defined by at least two opposing free edges, and which can occupy either a first, closed position or a second, open position. At the second end of the valve there are at least two flexible members attachable to an anterior and a posterior wall of a patient's blood vessel. A length of the orifice between said at least two opposing free edges when the orifice is generally closed is equal to about 1.5 to 2 times the diameter of a patient's blood vessel. Optionally, the two flexible members to a stent or tubular graft. The valved stent or tubular graft can be inserted into a patient's blood vessel or heart.

11 Claims, 16 Drawing Sheets

U.S. PATENT DOCUMENTS

| | | | |
|---|---|---|---|
| 7,452,371 B2 * | 11/2008 | Pavcnik et al. | 623/1.24 |
| 2001/0039450 A1 * | 11/2001 | Pavcnik et al. | 623/1.24 |
| 2003/0163194 A1 | 8/2003 | Quijano et al. | |
| 2003/0163195 A1 | 8/2003 | Quijano et al. | |
| 2003/0181974 A1 | 9/2003 | Xie et al. | |
| 2004/0117004 A1 | 6/2004 | Osborne et al. | |
| 2004/0138742 A1 | 7/2004 | Myers et al. | |
| 2005/0149181 A1 | 7/2005 | Eberhardt | |
| 2006/0167542 A1 | 7/2006 | Quintessenza | |
| 2006/0235511 A1 | 10/2006 | Osborne | |
| 2006/0253188 A1 | 11/2006 | Case | |
| 2007/0050014 A1 * | 3/2007 | Johnson | 623/1.24 |

OTHER PUBLICATIONS

Ran Gilad and Ron Somogyi, Percutaneous Heart Valves: The Emergence of a Disruptive Technology, Univ. of Toronto Medical J., vol. 82, No. 3 (May 2005), pp. 199-201.

* cited by examiner

BICUSPID VASCULAR VALVE AND METHODS FOR MAKING AND IMPLANTING SAME

CROSS-REFERENCE TO RELATED APPLICATIONS

This is a continuation-in-part of U.S. patent application Ser. No. 11/041,603, filed Jan. 24, 2005, now U.S. Pat. No. 7,320,705 which claims the benefit of U.S. provisional patent application No. 60/538,870, filed Jan. 23, 2004. The entire contents of both applications are incorporated herein by reference.

FIELD OF THE INVENTION

The invention relates generally to a tubular bicuspid vascular valve, which may be used as a heart valve, and to methods for making and implanting the valve. The valve has at least two flexible members that are attached to the wall of a blood vessel, such as a vein, or to a stent, and an orifice which is open when at rest, but is capable of collapsing to prevent reverse flow. The present invention provides a safe, relatively inexpensive, easily-constructed, effective and durable option for patients in need of vascular valves, and in particular, valves for right ventricular outflow tract reconstruction.

BACKGROUND OF THE INVENTION

Many patients who have had surgical reconstruction of the right ventricular outflow tract come back to the doctor in need of reoperative surgical reconstruction of the right ventricular outflow tract (RVOT). Typically there is a history of previously operated tetralogy of Fallot (TOF) or pulmonary stenosis (PS) with such patients. Tetralogy of Fallot is a heart problem that is characterized by four defects in the heart: 1) ventricular septal defect (VSD), which is a hole between the two bottom chambers of the heart; 2) pulmonary stenosis, or a narrowing at or slightly below the pulmonary valve; 3) positioning of the aorta over the ventricular septal defect; and 4) the right ventricle being unusually muscular.

The predominant physiologic abnormality is pulmonary insufficiency (PI), but varying degrees of RVOT obstruction may also be present. It is generally believed that patients tolerate PI reasonably well. In some, however, the long term effects of PI and subsequent right ventricle (RV) enlargement and dysfunction result in poor exercise tolerance and increased incidence of arrhythmias. Numerous surgical options are available for these patients; however, the optimal timing and specific valve used for reconstruction remain uncertain. Less than ideal experience with heterograft RVOT reconstruction stimulated interest into alternative materials and techniques. Favorable experimental and clinical experience with reconstruction using PTFE monocusp valves spurred an interest to consider a new method of reconstruction with this material.

Increasingly, over the last several years, concerns regarding post-operative pulmonary insufficiency or insufficiency/stenosis have emerged. The previous adage that pulmonary insufficiency after valvectomy and/or transanular patching during repair of TOF was well-tolerated is now being questioned. Recent studies with more refined methods of evaluation utilizing echocardiogram or magnetic resonance imaging (MRI), as well as exercise testing, clearly show there is a relationship between pulmonary insufficiency and volume overload that results in right ventricular enlargement and dysfunction. Symptoms resulting from physical exertion are late and usually follow these objective changes in ventricular dysfunction and size. Additionally, life threatening ventricular arrhythmias seem to be associated with the more severe cases of pulmonary insufficiency and ventricular changes.

There is good evidence that RV enlargement and dysfunction is reversible following pulmonary valve replacement (PVR). However, recent evidence shows that there is a lack of significant recovery of RV indices following PVR in adults with long-standing pulmonary insufficiency. Therefore, the timing of PVR is of major importance in the overall maintenance of ventricular function and optimal long-term outcomes. Additionally, a program of aggressive PVR in conjunction with intraoperative cryoblation is effective in reducing both the size of the heart chamber and the potential for lethal arrhythmias in TOF patients with severe pulmonary insufficiency. It is also useful in decreasing the QRS duration, wherein "QRS" is a complex of waves on an echocardiogram that represent the time it takes for the ventricles to depolarize—the normal length of time being between 40 milliseconds and 160 milliseconds. In general, indications for PVR are evolving but currently include patients with moderate-severe PI/PS and 1) exertional symptoms, class II or greater, 2) RV systolic dysfunction and/or enlargement, 3) decreased exercise tolerance 4) ventricular arrhythmias and/or QRS duration greater than 160 milliseconds.

There is considerable debate as to what type of valve or reconstruction is optimal for the pulmonary position. A vast array of materials and methods have been utilized. Recent studies support the use of homografts, replacement valves from human donors, as well as stented and unstented heterograft valves, valves from non-human donors (pig valves are commonly used). However, despite definite early patient improvement, all reports for use of biologic valves show a significant incidence of recurrent valvar insufficiency and/or obstruction. A recent study of thirty-six patients utilizing homografts and heterografts for PVR noted that nine out of the thirty-four patients that were followed-up developed moderate to severe PI, and seventeen out of thirty-four developed significant obstruction within 80 months follow-up. Similarly, within 4.9 years, the incidence of homograft insufficiency was 50% mild, and 28% moderate-severe. Recent evidence suggests an immunologic basis for this early graft failure pattern.

In light of the above, it was thought that a non-immunologic, non-degenerating, and relatively durable material, such as PTFE, and a different method of insertion of the valve would provide more optimal results. Experience from 3-17 years utilizing a PTFE monocusp for RVOT reconstruction suggests reasonable long-term durability and freedom from degeneration. A larger study of 158 patients using a PTFE monocusp for RVOT reconstruction, with follow-up from 6 months to 8 years, demonstrated no stenosis, calcification, or embolization. There was, however, significant development of pulmonary insufficiency graded as moderate to severe by 35 months in this monocusp study.

The prior art discloses many types of heart valves, such in U.S. Pat. No. 5,344,442 issued to Deac, which discloses a cardiac valve designed to replace defective mitral valves in a patient's heart that comprises a plurality of flexible trapezoidal membranes each joined to another trapezoidal membrane to form a frustoconical annular body. Also, U.S. Pat. No. 4,340,977 issued to Brownlee, et al. for a catenary mitral valve replacement, which includes a mitral valve comprising a stent with a circular base and two upstanding, diametrically opposed struts that separate a pair of diametrically opposed arcuately shaped depressed reliefs. U.S. Pat. No. 5,500,015 issued to Deac for a cardiac valve comprising a plurality of membranes; U.S. Pat. No. 4,790,844 issued to Ovil, for a cardiac valve with an annular body having a bishop's miter shape with a cylindrical end and a pair of diametrically opposed triangular flap portions extending therefrom, and when the valve is inserted, the mitered end is free and the cylindrical end is attached to heart tissue; U.S. Patent Application Publication No. US2003/0181974 A1, filed by Xie, et al. for a bioprosthesis and method for suturelessly making same, which discloses a diamond-shaped frame to which a membrane is attached and wherein the frame is folded on itself and a slit cut into the folded side to allow fluid to flow through it; U.S. Pat. No. 6,682,559 B2, issued to Myers, et al. for a prosthetic heart valve that discloses a valve that includes a plurality of leaflets that are sewn together creating an annular structure which is then sutured into the heart; U.S. Patent Application Publication No. US2003/0163195 A1, filed by Quijano, et al. for a stentless atrioventricular heart valve fabricated from a singular flat membrane, which discloses attaching a membrane to a circumferential valve ring wherein the ring is sutured into an atrioventricular junction of a patient's heart.

There is also a need for low cost, safe valves for use in other parts of the vascular system such as the veins.

SUMMARY OF THE INVENTION

In an aspect of the present invention, a vascular valve constructed from a biocompatible material that is designed to be surgically implanted in a patient's blood vessel, such as the right ventricular outflow tract. The valve can include a generally tubular flexible element with first and second ends. The first end is an orifice defined by at least two opposing free edges, and which can occupy either a first, closed position or a second, open position. The second end comprises at least two flexible members attachable to an anterior and a posterior wall of a patient's blood vessel such that the flexible element retains its generally tubular form and such that the orifice may open and close with the flow of blood. A length of the orifice between said at least two opposing free edges when the orifice is generally closed is equal to about 1.5 to 2.0 times the diameter of a patient's blood vessel.

In further aspects, the vascular valve further includes an outer tubular structure. The flexible members are attached to the outer tubular structure such that the tubular element is disposed within the outer tubular structure. In detailed aspects, the tubular structure includes either a stent, a graft tube, or both a stent and a graft tube.

In another aspect of the present invention, a method of making a vascular valve includes measuring the diameter of a patient's blood vessel into which the valve is to be implanted, and cutting from a flat sheet of flexible synthetic biocompatible material a generally elliptical shape having a major and a minor axis, wherein the minor axis has a predetermined length and is defined by at least two peripheral edges. The method further includes incising said elliptical shape along the minor axis, such that said incision extends along the minor axis for a distance approximately equal to 1.5 to 2.0 times the measured diameter of the patient's blood vessel, and is defined by said at least two peripheral edges, and folding said elliptical shape in half on itself along said minor axis to form two flexible members from the ends of the elliptical shape. The incision is formed into an orifice of predetermined diameter and shape such that the flexible biocompatible material sheet forms a generally tubular shape with said incision at one end thereof forming an orifice that can open and close when inserted into the patient's blood vessel.

In other aspects, the method further comprises attaching each of the flexible members to a stent or a graft tube. The stent or the graft tube is sized for insertion into the patient's blood vessel, such that the flexible members are generally parallel to each other, and such that said generally tubular structure is maintained to form a valve.

In still another aspect of the present invention, a method of treating vascular or heart disease includes making an incision into a blood vessel of a patient, measuring the diameter of the patient's blood vessel, and cutting from a flat sheet of flexible synthetic biocompatible material a generally elliptical shape having a major and a minor axis, wherein the minor axis has a predetermined length and is defined by at least two peripheral edges. The elliptical shape is incised along the minor axis, such that said incision extends along the minor axis for a distance approximately equal to 1.5 to 2.0 times the measured diameter of the patient's blood vessel, and is defined by said at least two peripheral edges. The elliptical shape is folded in half on itself along said minor axis to create at least two flexible members. The method further includes forming said incision into an orifice of predetermined diameter and shape such that the flexible synthetic resin sheet forms a generally tubular shape with said incision at one end thereof forming an orifice that can open and close when inserted into the patient's blood vessel, and attaching each of said flexible members to the anterior and posterior wall of the patient's blood vessel, such that said flexible members are generally parallel to each other, and such that said generally tubular structure is maintained.

In yet a further arrangement, the invention provides a method of treating vascular or heart disease including measuring the diameter of the patient's blood vessel, cutting from a flat sheet of flexible synthetic biocompatible material a generally elliptical shape having a major and a minor axis, wherein the minor axis has a predetermined length and is defined by at least two peripheral edges, and incising said elliptical shape along the minor axis, such that said incision extends along the minor axis for a distance approximately equal to 1.5 to 2.0 times the measured diameter of the patient's blood vessel, and is defined by said at least two peripheral edges. The elliptical shape is folded in half on itself along said minor axis to create at least two flexible members. The incision is formed into an orifice of predetermined diameter and shape such that the flexible synthetic resin sheet forms a generally tubular shape with said incision at one end thereof forming an orifice that can open and close when inserted into the patient's blood vessel. The method further includes attaching each of said flexible members to a stent sized for insertion into the patient's blood vessel, such that said flexible members are generally parallel to each other, and such that said generally tubular structure is maintained to form a valve, and inserting the stent containing the valve into the patient's blood vessel, and attaching the stent to the blood vessel walls.

In another arrangement, the invention provides a method of surgically reconstructing a right ventricular outflow tract of a patient, including making an incision into the right ventricular outflow tract, measuring the diameter of the right ventricular outflow tract, cutting from a flat sheet of flexible synthetic biocompatible material a generally elliptical shape having a major and a minor axis, wherein the minor axis has a predetermined length and is defined by at least two peripheral edges, and incising said elliptical shape along the minor axis, such that said incision extends along the minor axis for a distance approximately equal to 1.5 to 2.0 times the measured diameter of the patient's right ventricular outflow tract, and is defined by said at least two peripheral edges. The method further includes folding said elliptical shape in half on itself along said minor axis, forming said incision into an orifice of predetermined diameter and shape such that the flexible synthetic resin sheet forms a generally tubular shape with said incision at one end thereof forming an orifice that can open and close when inserted into the patient's blood vessel, and suturing each of said plurality of flexible members to the anterior and posterior wall of the infundibular septum of the right ventricular outflow tract, such that said flexible members are generally parallel to each other, and such that said generally tubular structure is maintained, whereby the valve is held in place in the right ventricular outflow tract and the orifice can open and close with the flow of blood through the right ventricular outflow tract.

BRIEF DESCRIPTION OF THE DRAWINGS

A particularly preferred embodiment of the invention of this apparatus will be described in detail below in connection with the drawings in which.

Figure 1:
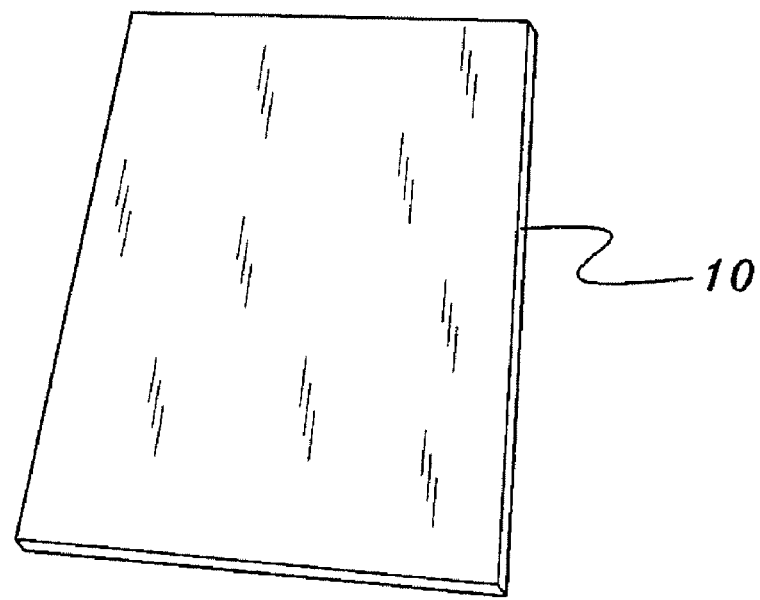
FIG. 1 is a flat sheet of PTFE material from which the a preferred embodiment will be crafted.

A particularly preferred embodiment of the present invention is illustrated in the drawings.

DESCRIPTION OF PREFERRED EMBODIMENTS

A preferred embodiment of the present invention comprises a vascular valve 10 that is constructed from a synthetic, non-degradable, durable, safe, biocompatible and non-thrombogenic material, such as PTFE or another fluoropolymer, a PET such as Dacron® or the like, GORE-TEX®, Teflon®, or other synthetic resin or other biocompatible material suitable for use in biologic applications, and a method for making and inserting the vascular valve. The biocompatible material may be initially provided in the form of a sheet, and may have any suitable size or thickness. An appropriate thickness in some arrangements, depending on the size of the blood vessel the valve is to be implanted into, and the type of material, ranges from 0.1 mm to 0.6 mm. A synthetic material is preferred because there is no need for the patient to use anti-rejection drugs, and because such materials are well tolerated by the body.

Figure 6:
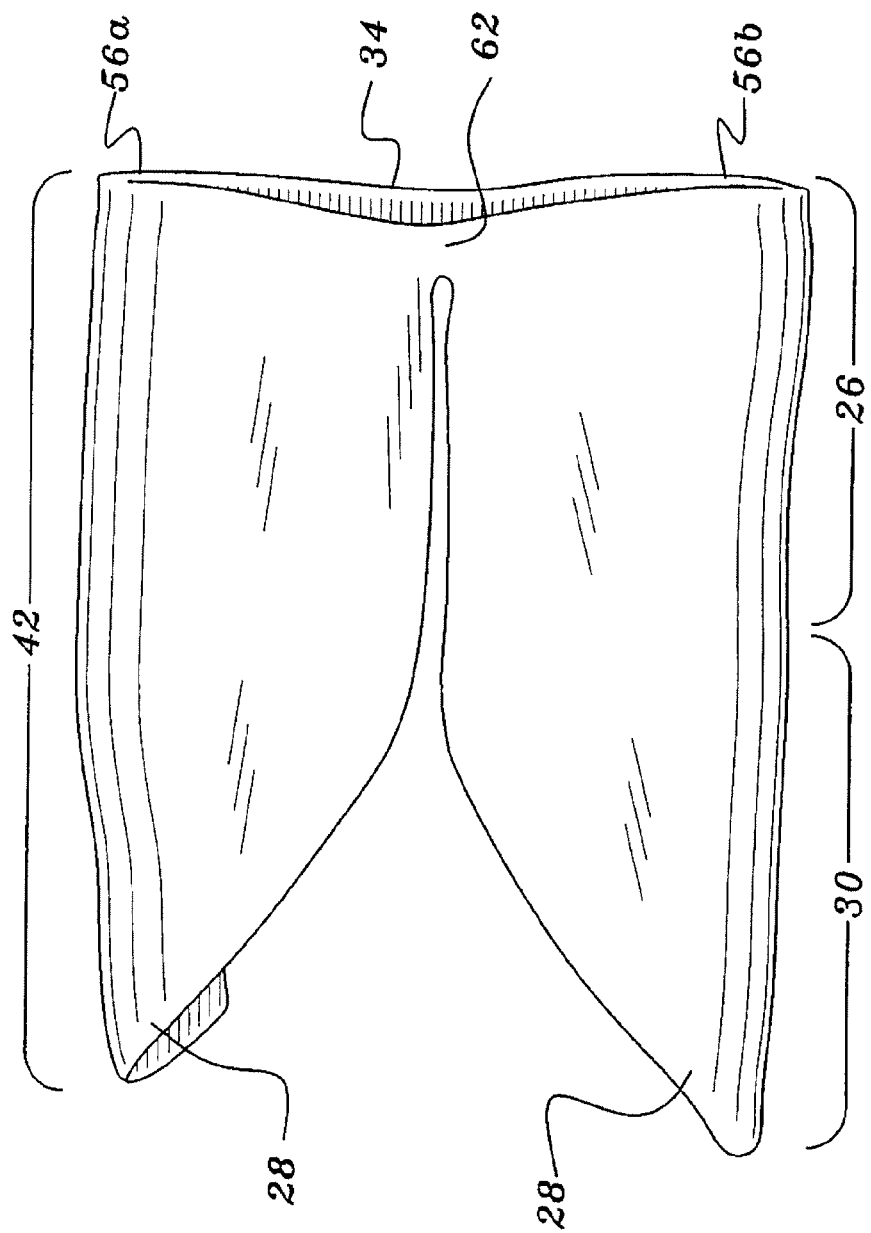
FIG. 6 shows a horizontal view of the preferred embodiment.
Figure 7:
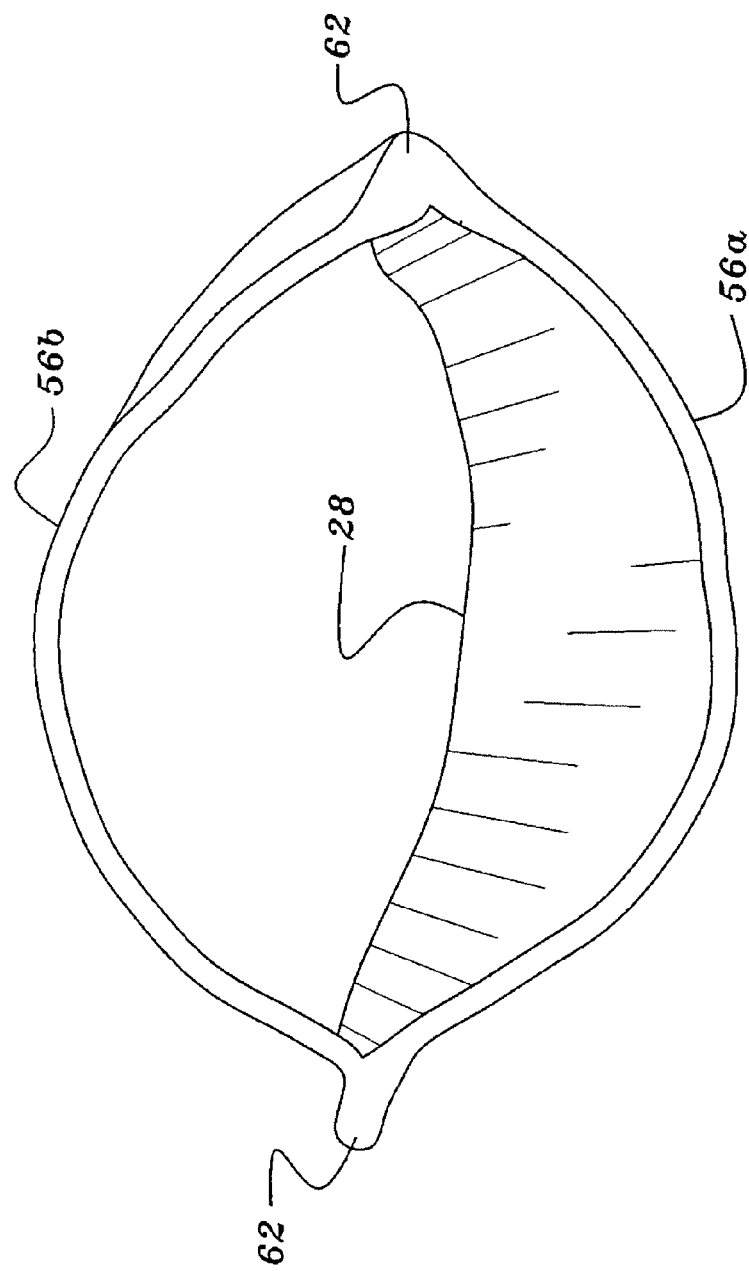
FIG. 7 shows a longitudinal view of the preferred embodiment.
Figure 8:
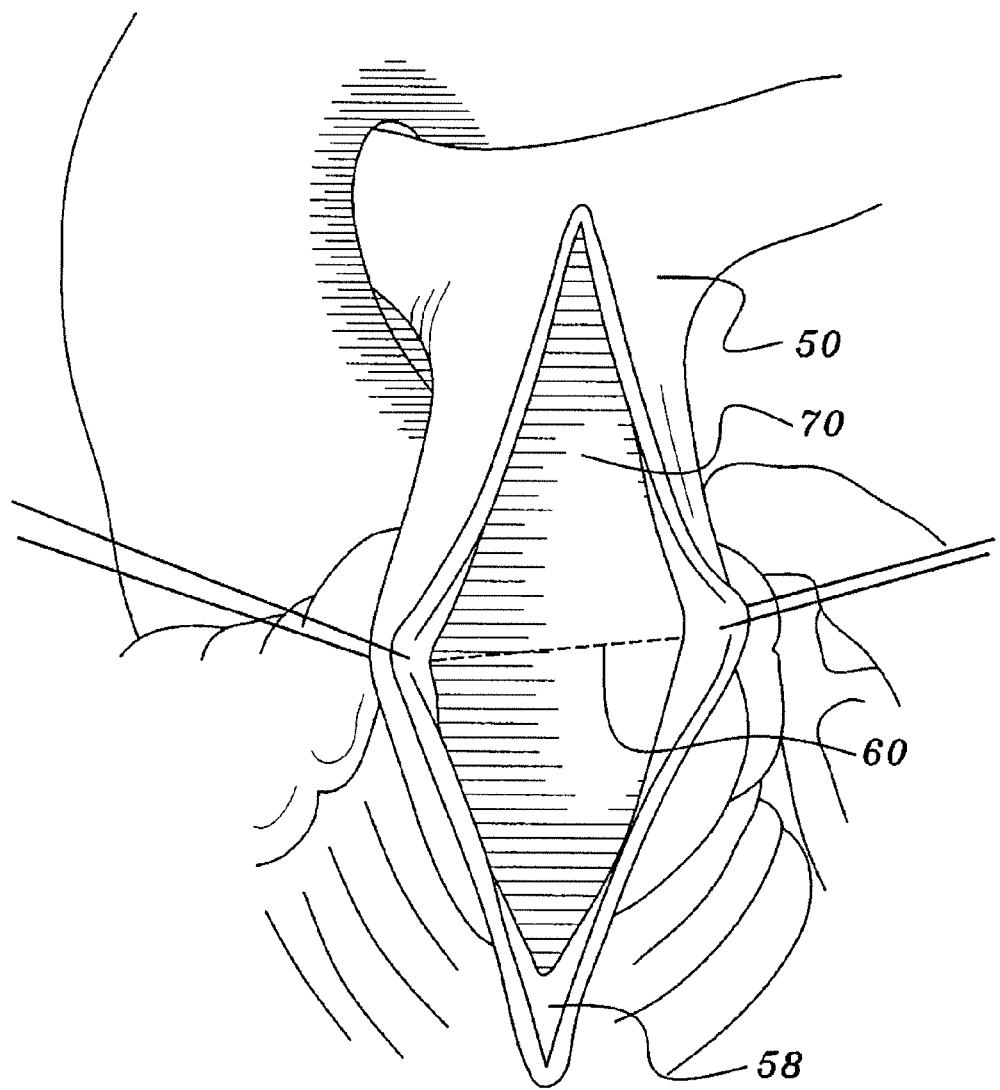
FIG. 8 depicts the incision in the right ventricular outflow tract into which the preferred embodiment will be inserted.
Figure 9:
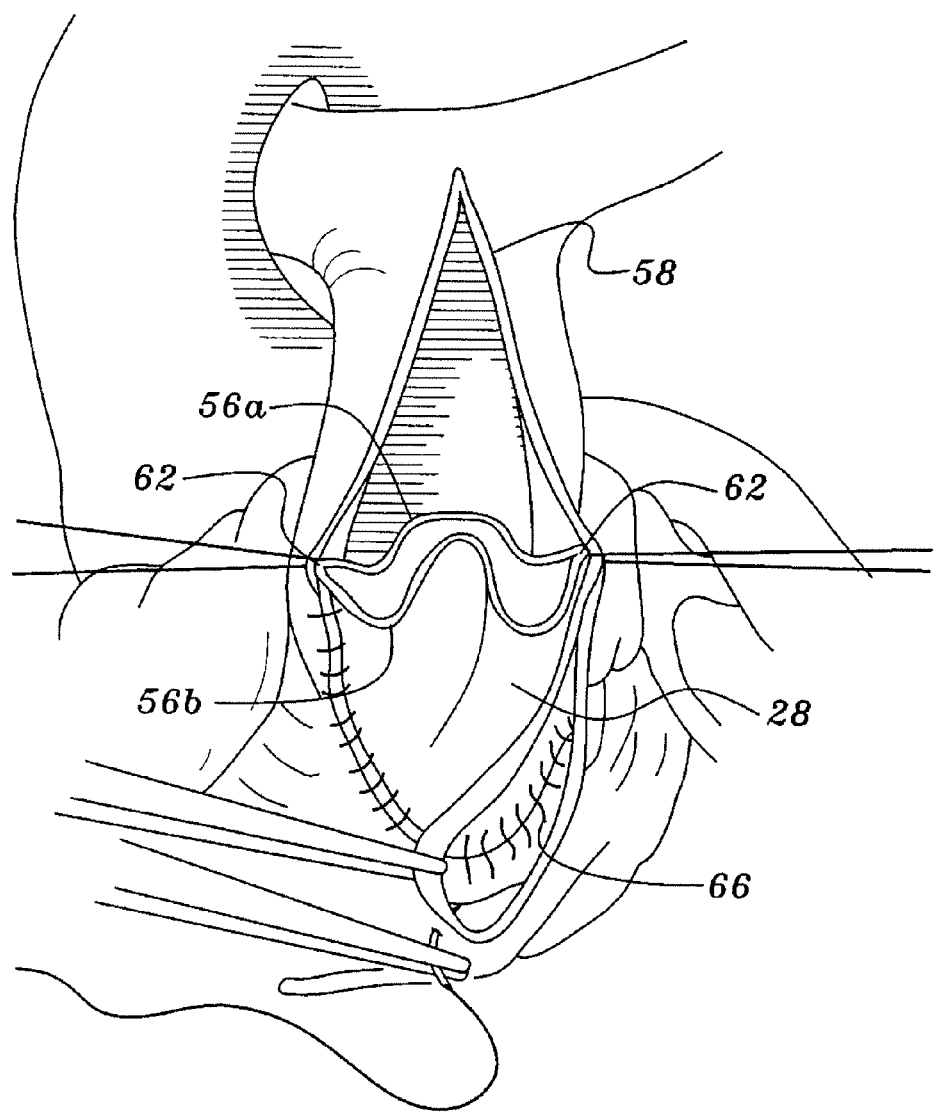
FIG. 9 depicts the preferred embodiment being sewn into place.
Figure 10:
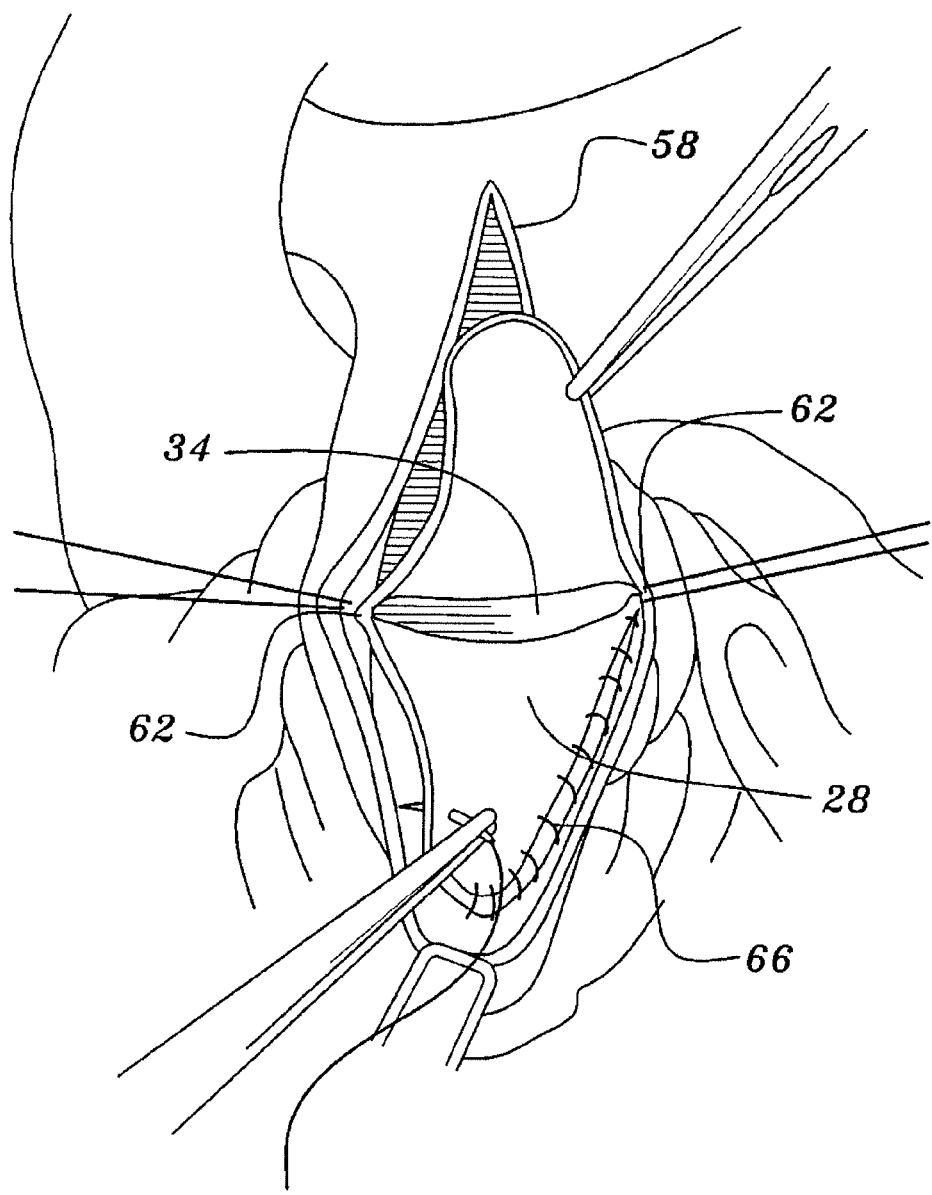
FIG. 10 depicts the preferred embodiment being sewn into place.
Figure 11:
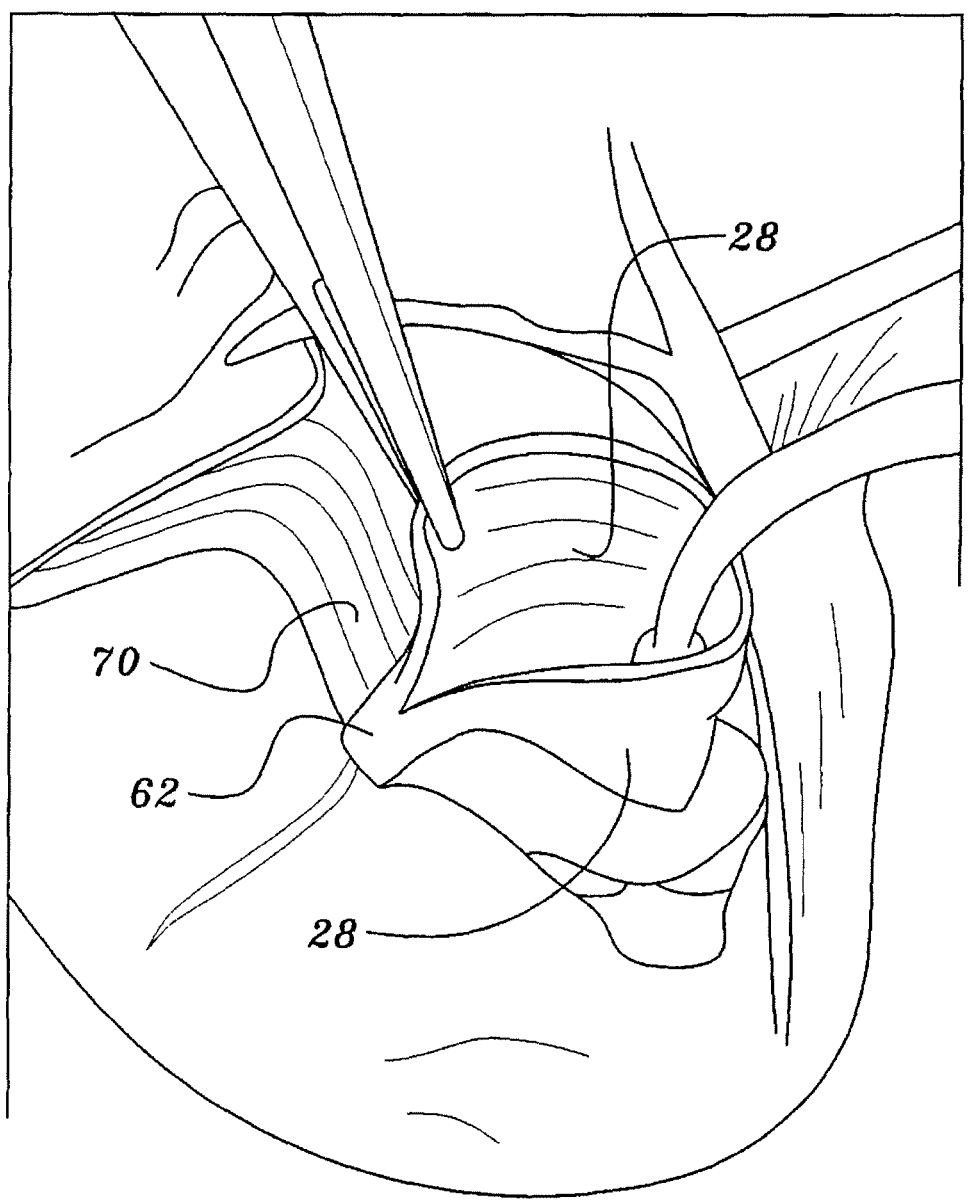
FIG. 11 shows the actual placement of the preferred embodiment into a heart while the valve is in the open position.
Figure 12:
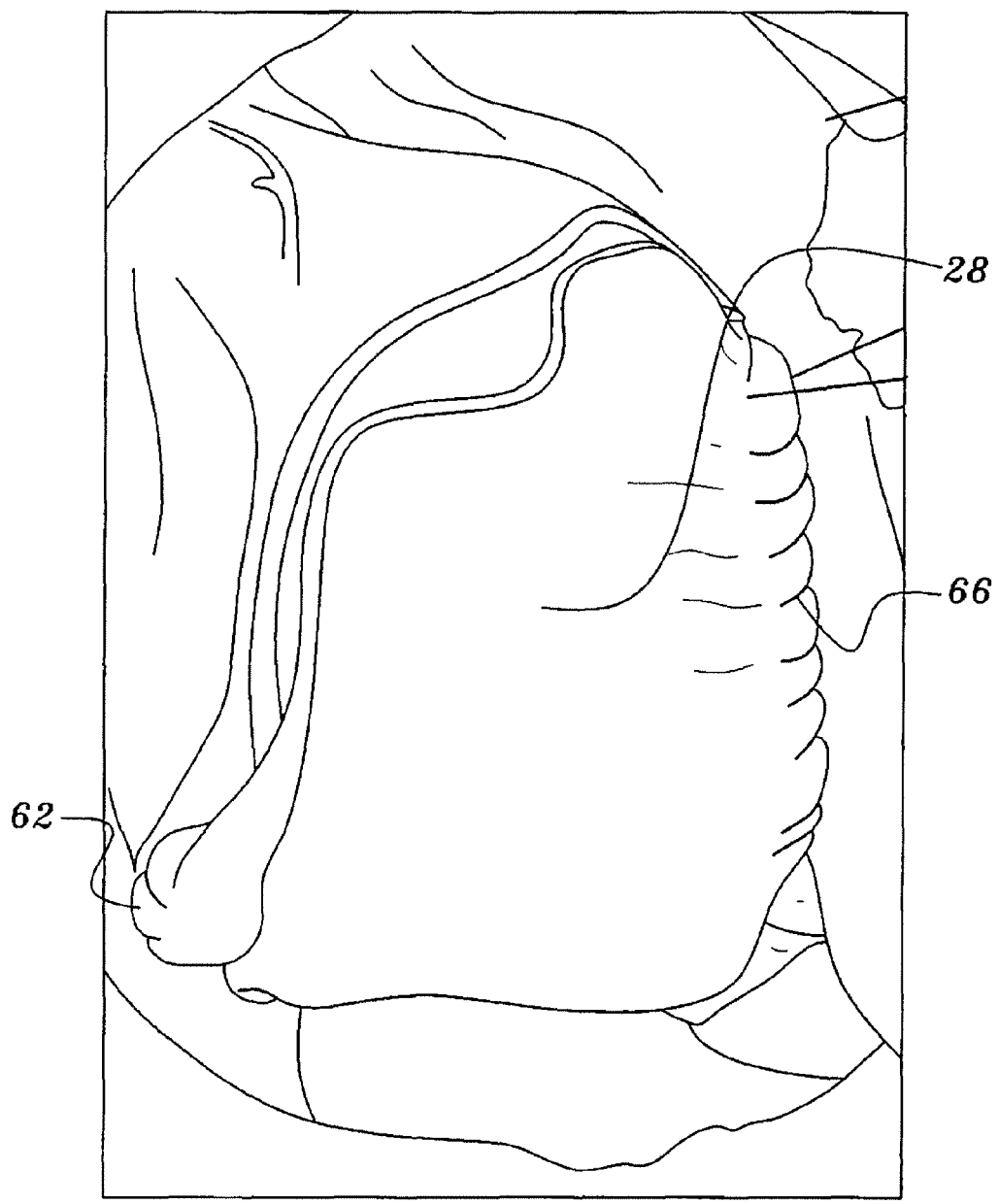
FIG. 12 shows the actual placement of the preferred embodiment into a heart while the valve is in the generally closed position.
Figure 13:
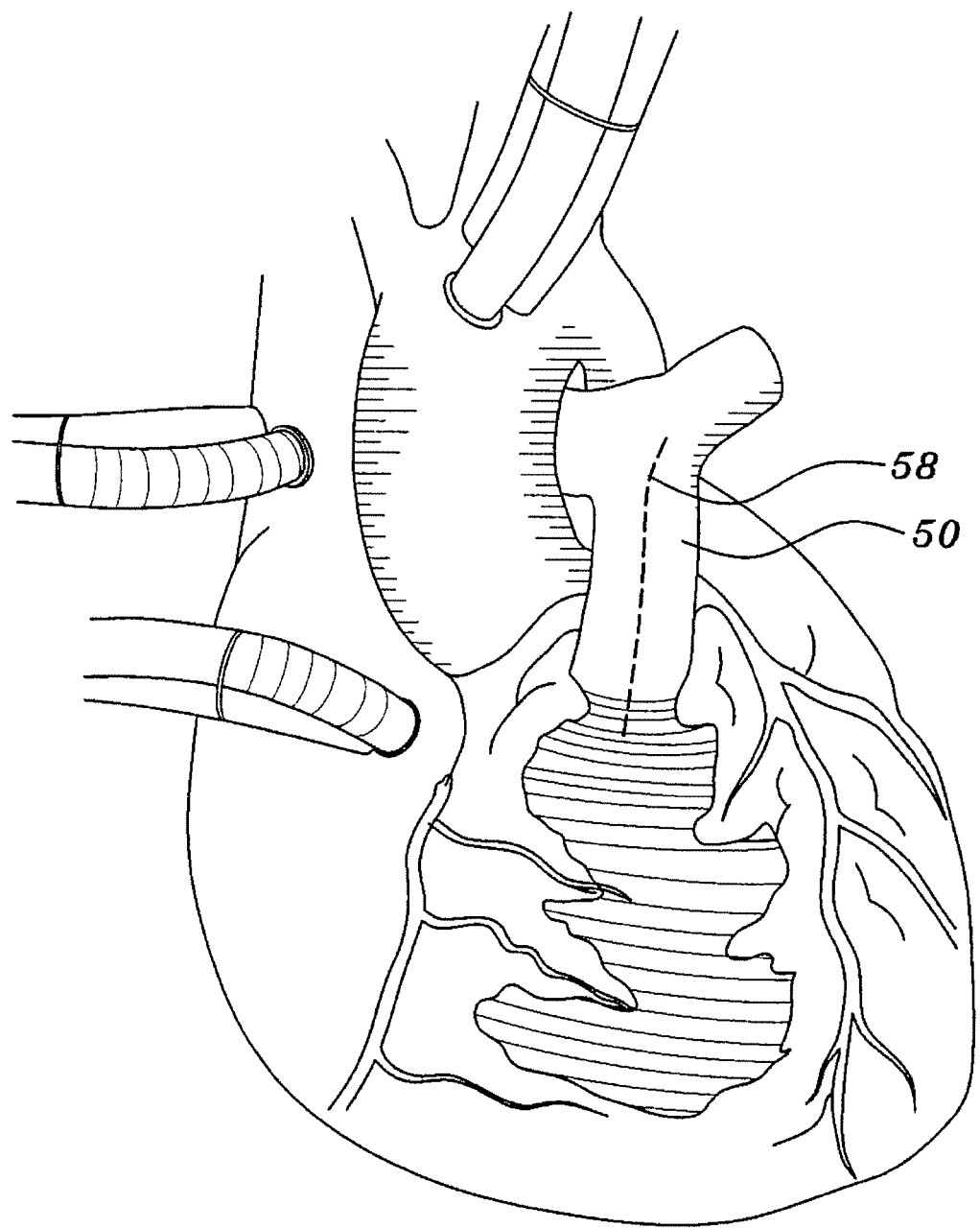
FIG. 13 is an illustration of the human heart, showing a dashed line where the incision into the right ventricular outflow tract is to be made.
Figure 14:
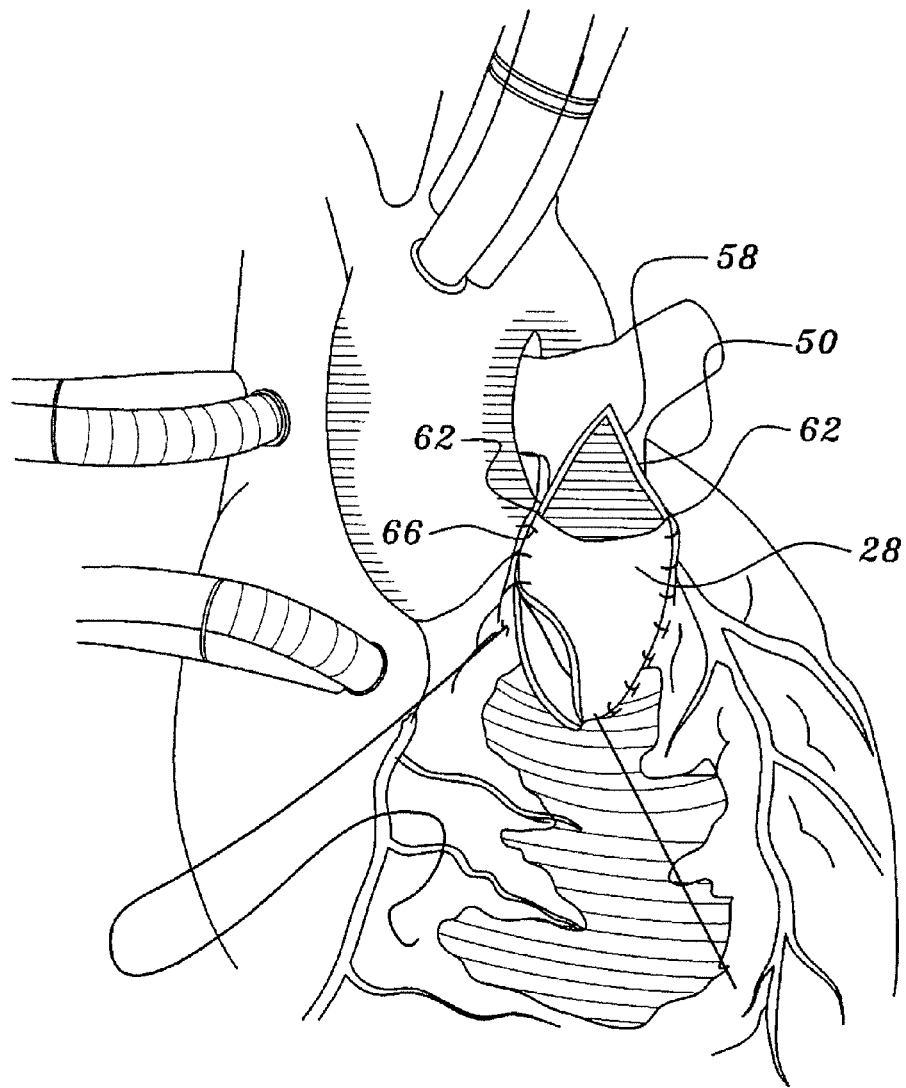
FIG. 14 is an illustration of the human heart into which the preferred embodiment is being sewn.

A preferred embodiment of the present invention is shown in FIGS. 6 and 7, and comprises a generally tubular element 42 with a first end 26 and a second end 30, wherein the first end 26 comprises a generally circular orifice 34 defined by at least two opposing free edges 56a, 56b of a predetermined length, and the second end 30 comprises a plurality of flexible members 28. Two flexible members 28 are shown in the figures, which have a generally parabolic shape. It will be appreciated that other shapes may be used for the flexible members 28, such as a triangular shape, a catenary arch shape, a generally curved shape that is pointed at the end such as a bishop's miter shape, etc. The flexible members may be split into different sections, for example, a generally V-shaped groove may be cut into each flexible member 28 such that the flexible member has two prongs or legs that can extend along the blood vessel. The orifice 34 can occupy either of two positions, one being flat and generally closed (FIG. 12), the second being generally circular and open (FIG. 11). The predetermined length of an incision 16 between the two opposing free edges 56a, 56b of the orifice 34 can be about 1.5 times the diameter 60 of a patient's right ventricular outflow tract 50 or other blood vessel, but may be between 1.5 and 2.0 times the diameter of the blood vessel.

Figure 2:
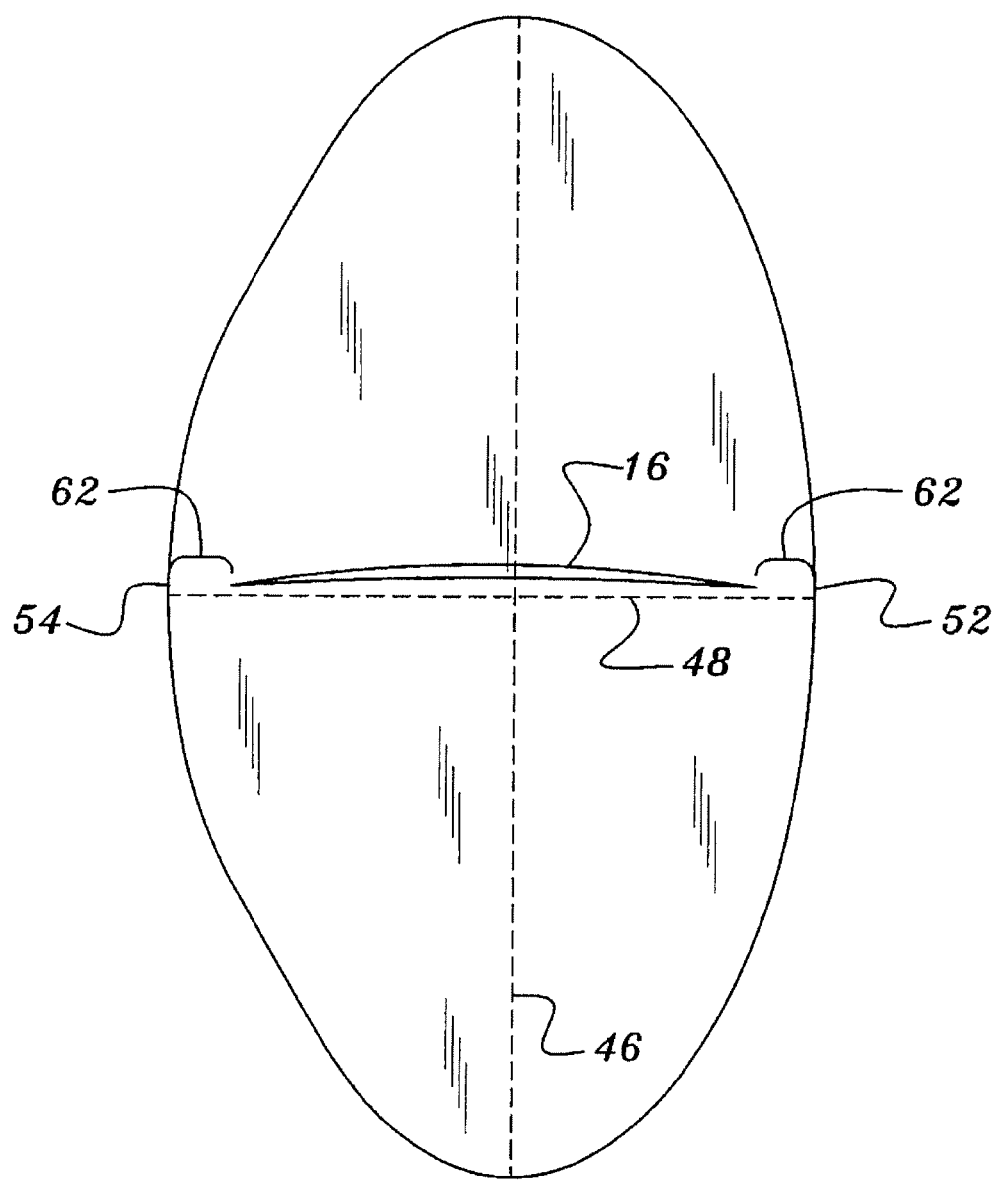
FIG. 2 is an ellipse that has been cut out from the flat sheet.

The present invention also encompasses a method of making the vascular valve 10, shown in FIGS. 8-14, which comprises the steps of making an incision 58 into the right ventricular outflow tract 50 or other blood vessel into which the vascular valve is to be implanted and measuring the diameter 60 of the right ventricular outflow tract or other blood vessel. It will be appreciated that the measurement of the diameter of the blood vessel can be carried out in a non-invasive manner prior to making an incision in the vessel. For example, the measurement may be made using ultrasound, MRI or other images of the vessel. Then, from a flat sheet of biocompatible material 10 (FIG. 1), which may be a synthetic, non-degradable, durable, safe, synthetic resin material, such as a fluoropolymer like PTFE, a PET such as Dacron® or the like, GORE-TEX®, Teflon®, or other synthetic resin or other biocompatible material suitable for use in biologic applications, a generally elliptical shape 22 (FIG. 2), with a minor axis 48 and a major axis 46, is cut. The minor axis 48 is defined by first 52 and second 54 edges. Although the shape of the material 10 used in the illustrated embodiment is described as an ellipse, any suitable shape may be used. Other Exemplary shapes that may be employed include a diamond shape, or a shape may be cut comprising two parabolic curves, two bishop's miter shaped curves, two catenary curves or two other similar curves, joined at their widest points.

Figure 3:
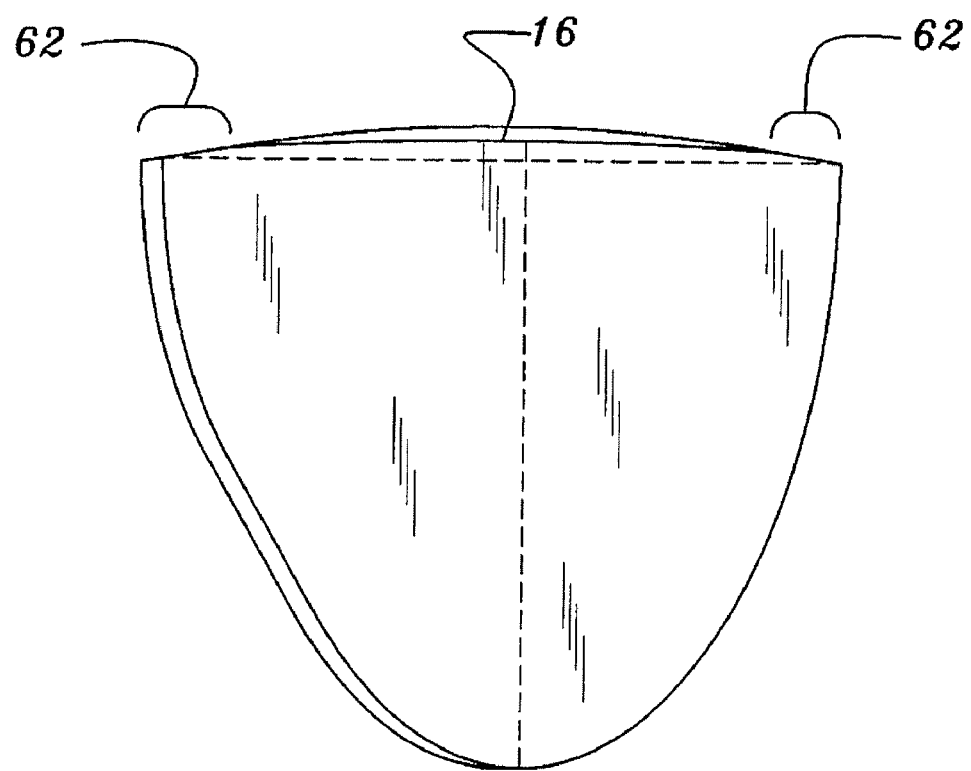
FIG. 3 is the ellipse, shown folded in half, with the fold defining one end.
Figure 4:
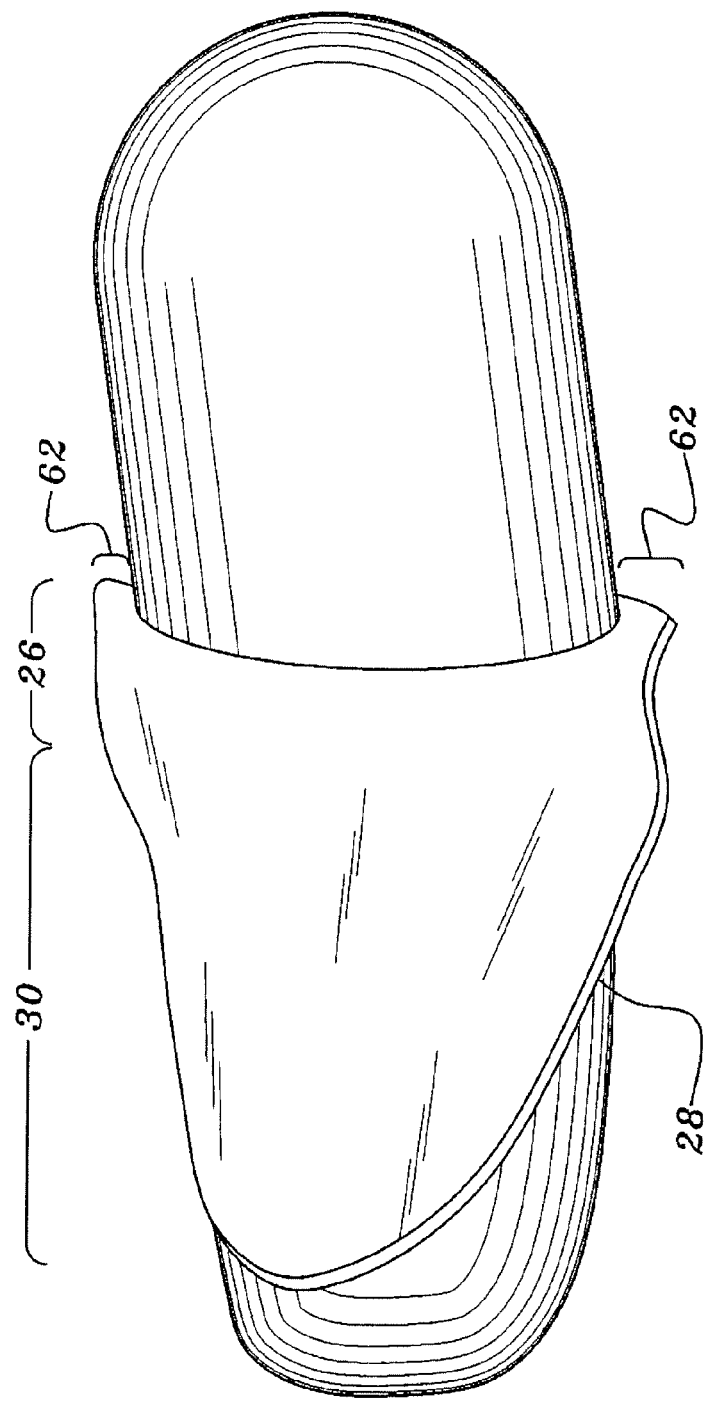
FIG. 4 is a top elevation a preferred embodiment being sized with a sizing tool.
Figure 5:
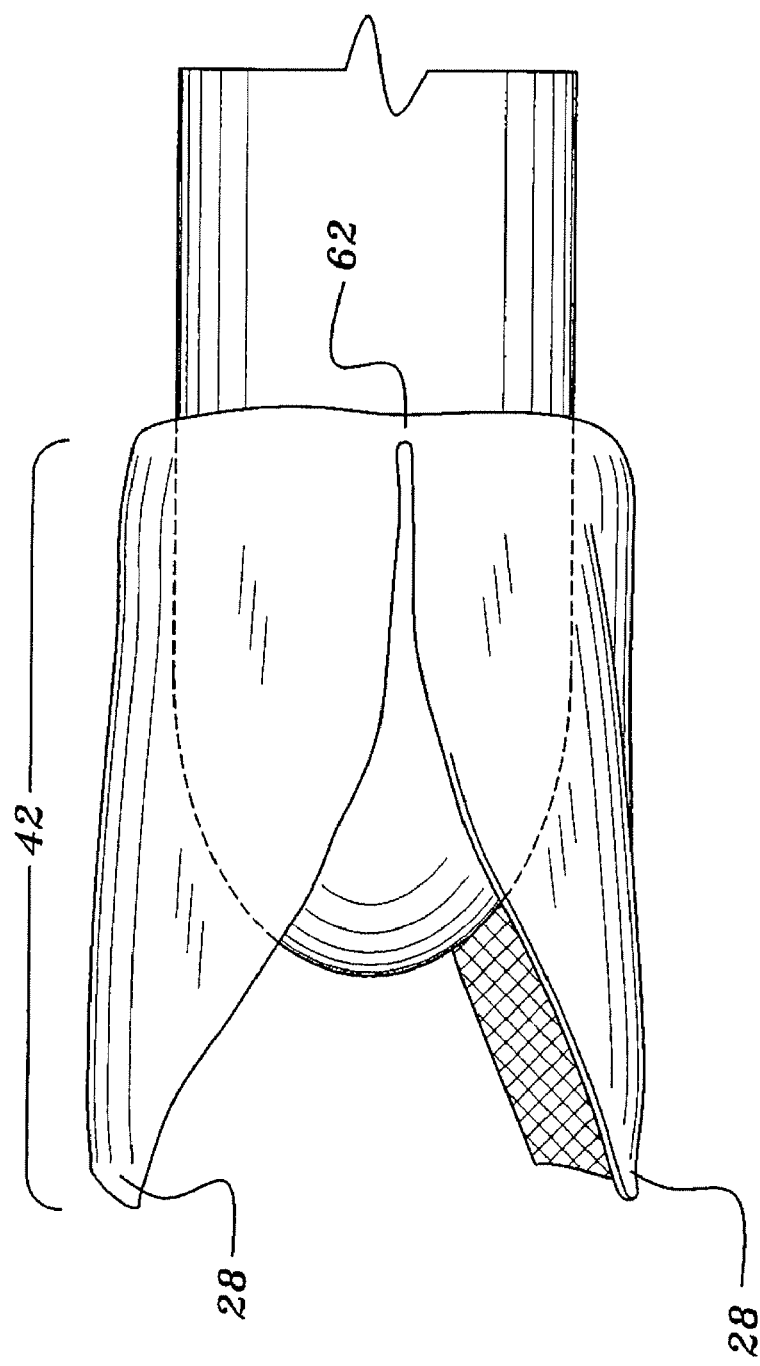
FIG. 5 is a side view of a preferred embodiment being sized with a sizing tool.

The ellipse 22 is incised along the minor axis 48, creating an incision 16 which extends along the minor axis 48 for a predetermined length. The predetermined length measures about 1.5-2.0 times the diameter 60 of the patient's right ventricular outflow tract 50 or other blood vessel, and extends between two peripheral edges 62 starting at about 2 mm from the first edge 52, and ending at about 2 mm from the second edge 54 of the ellipse shape 22, defining the two peripheral edges 62 to the orifice 34. The length of the peripheral edges 62 can vary, depending on the size of the valve that is being created. For example, the peripheral edges may be between 1 mm and 3 mm. The ellipse 22 or other shape that is cut from the biocompatible material 10 is then folded in half on itself (FIG. 3) along the minor axis 48 such that the incision 16 may be formed (FIGS. 4-5) into a generally circular orifice 34 (FIG. 6-7) of a predetermined size, and such that the ends of the ellipse form the flexible members 28 extending from the orifice 34. Alternatively, the ellipse 22 or other suitable shape may be cut by first folding the sheet of biocompatible material 10 in half, cutting half an ellipse or a bishop's miter or other similar shape, and then incising along the crease, and refolding to form the valve. It will be appreciated that as the biocompatible material 10 is entirely flexible, and as there are no frame members around the valve, the orifice 34 can open and close easily in response to the flow of blood through the blood vessel.

The invention also contemplates a method of insertion (FIGS. 8-14) of the vascular valve into a patient's blood vessel to treat disease, and in particular contemplates the use of the valve as a heart valve for insertion into the patient's right ventricular outflow tract. The method can include the steps of making an incision 58 in the right ventricular outflow tract 50 or other blood vessel and attaching each of the flexible members 28, conveniently via sutures 66, to the anterior and posterior walls of the infundibular septum 70 of the right ventricular outflow tract 50 (or the anterior and posterior walls of the blood vessel into which the valve is being implanted), such that the flexible members 28 are generally parallel to each other, and such that a generally tubular configuration is maintained (FIG. 11).

When inserted into the patient's right ventricular outflow tract, or other blood vessel, the generally tubular configuration enables the incision to extend across the right ventricular outflow tract or other part of the vasculature, such that the incision 16 can be formed into the generally circular orifice 34 when blood is flowing through the RVOT or vessel. The orifice 34 can thus close into the generally flat and closed position to prevent backflow as the blood flow ceases or slightly reverses as the patient's heart beats. Thus, the valve has a generally one-way function. The flexible members 28 hold the valve in position, because they are sutured to the walls of the blood vessel or infundibular septum 70, and prevent it from becoming dislodged in use.

Figure 15:
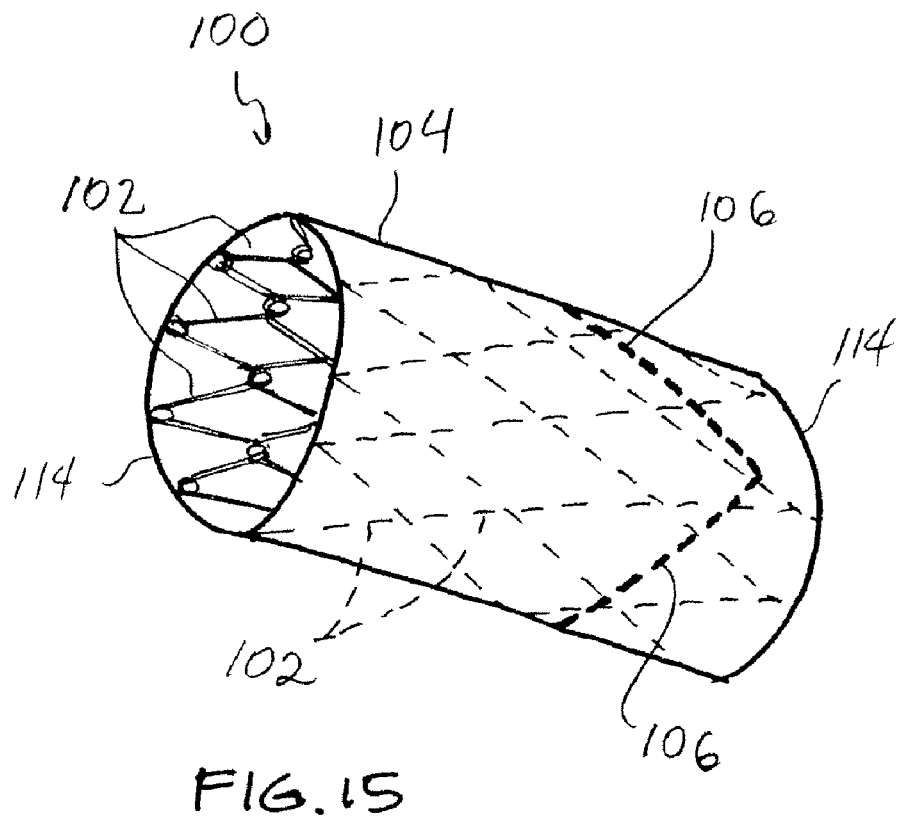
FIG. 15 is a perspective view of a further embodiment of the present invention, showing a bicuspid valve sutured to a tube having inner surfaces supported by wires.
Figure 16:
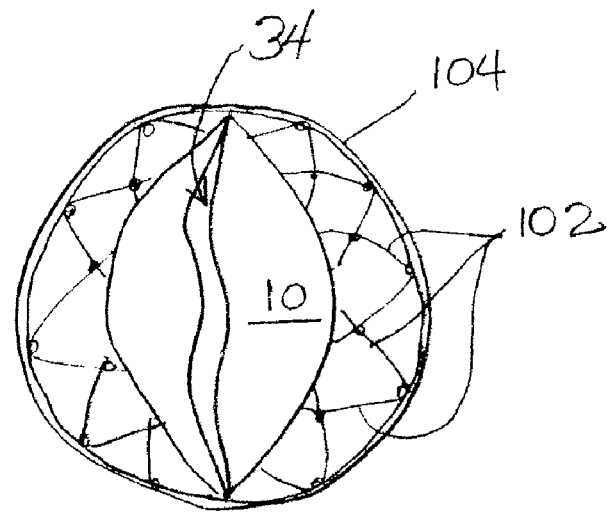
FIG. 16 is an end view of the embodiment of FIG. 16, showing moveable portions of the bicuspid valve in a partially open configuration.

Referring next to FIGS. 15 and 16, a valve 10 may be provided in a stent 100. The valve 10 can be formed in a manner described above in connection with FIGS. 1-3. In the illustrated embodiment, the stent 100 is formed of a plurality of interlocking wires 102 that are bent into v-shaped or diamond shaped formations. The wires 102 are covered with a sheet of biocompatible material 104, which can be a synthetic material and is preferably the same material that the valve 10 is formed from. The biocompatible material 14 is wrapped around the stent 100 to form a flexible tube, such as a graft tube. Inner surfaces of the flexible tube are supported by the wires 102. The flexible members of the valve 10 are stitched into the biocompatible material 104 with sutures 106. In this way, the valve orifice 34 extends across the lumen of the flexible tube. The valve 10 may also be bonded to the biocompatible material 104 with adhesives or heat. It will be appreciated that other stent strut geometries, patterned differently than what is shown in FIGS. 15 and 16, can be used to support the graft tube and the valve 10.

Optionally, needle-like prongs may be provided (not shown), emerging from either the outlet or inlet ends 114, or both ends, to allow secure fixation to the heart or vasculature within which it is deployed. The valve 10 may be implanted using a self-expanding or balloon expandable stent for percutaneous or transvenous implantation into the heart or other vascular structure. An additional balloon expanding stent may be attached to allow adequate tissue pressure and fixation as a means of maintaining a stable position within the heart or vasculature.

Figure 17:
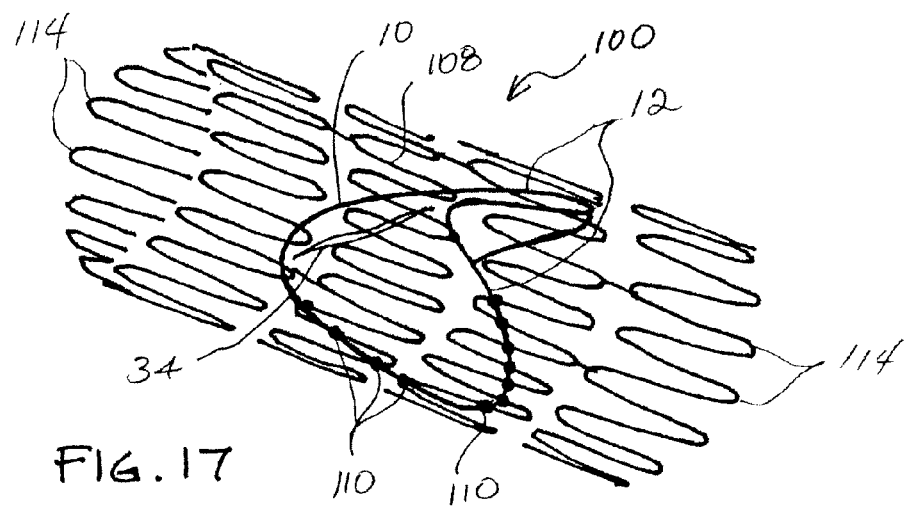
FIG. 17 is a perspective view of an embodiment of the present invention, showing a bicuspid valve disposed within a stent and attached to stent struts.

Referring next to FIG. 17, a valve 10 can be provided within a stent 100 that is not covered with a graft tube. The valve 10 can be formed in a manner described above in connection with FIGS. 1-3. The flexible members 28 of the valve 10 are attached to the stent struts 108 by means of sutures 110, adhesives, or other methods. In this way, the orifice 34 of the valve 10 can move between open and closed positions. The flexible members 28 have outer edge regions with no frame structure, which facilitates suturing of the outer edge regions to the stent 100. It will be appreciated that other types of wire structures, configured differently than what is shown in FIG. 17, can be used.

Figure 18:
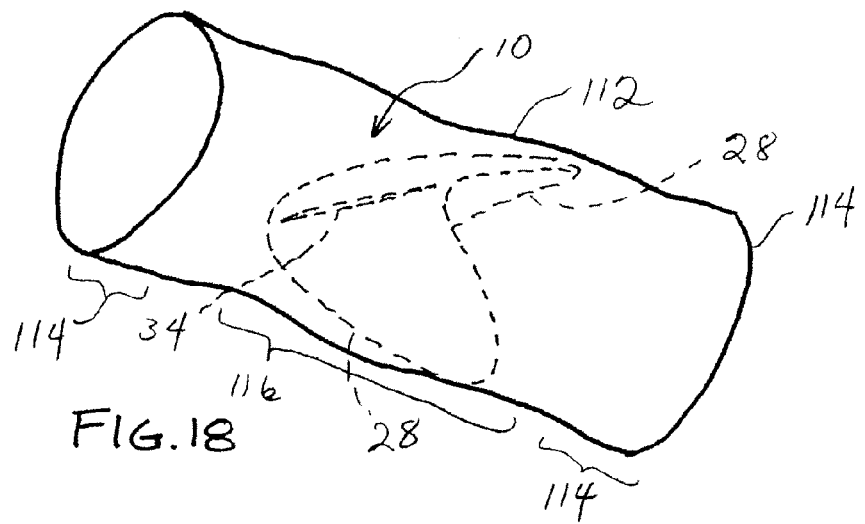
FIG. 18 is a perspective view of an embodiment of the present invention, showing a bicuspid valve disposed within and attached to a graft tube.

Referring next to FIG. 18, a valve 10 can be disposed within a graft tube 112 made of a biocompatible material. The biocompatible material can be a synthetic material, such as Dacron® or GORE-TEX®, and can be the same type of sheet material used to make the valve 10. The valve 10 has the same structure as the valve shown in FIGS. 1-3 and can be formed in the same manner described above in connection with FIGS. 1-3. The flexible members 28 of the valve 10 are attached to the inner surface of the graft tube by means of sutures, adhesives, heat bonding, or other methods. In the illustrated embodiment, the valve 10 is located in a medial portion 116 of the graft tube 112, away from the edge portions 114. In other embodiments, the valve 10 can be located at or adjacent to either one or both of the edge portions 114.

The covered stent (FIGS. 15-16), uncovered stent (FIG. 17) or graft tube (FIG. 18) containing the valve 10 can be implanted in a patient by various means. For example, they can be inserted into a blood vessel using a peripheral transvenous catheter technique, as previously mentioned. The stent 100 and the valve 10 can be crimped to a sufficiently small outer diameter to allow for peripheral transvenous catheter delivery of the stent 100. When delivered through a bodily lumen to a desired anatomical site using a catheter, the stent 100 self-expands upon removal of the catheter from the stent or the stent can be expanded by inflating an underlying balloon on the catheter. When expanded, the stent 100 forms a generally tubular structure, such as shown in FIGS. 15-17.

The covered stent (FIGS. 15-16), uncovered stent (FIG. 17) or graft tube (FIG. 18) can also be inserted into or attached to a patient's heart using a limited surgical access technique or an open surgical procedure. End portions 114 of the stent 100 or graft tube 112 can be sutured to a patient's heart, blood vessel, or other organ depending on medical need.

While the foregoing describes particularly a preferred embodiment of the method and apparatus of this invention, it is to be understood that this embodiment is illustrative only of the principles of this invention and is not to be considered limitative thereof. Because numerous variations and modification of the apparatus and method of this invention will readily occur to those skilled in the art, the scope of this invention is to be limited solely by the claims appended hereto.

The invention claimed is:

1. A vascular valve comprising:
   a generally tubular element with first and second ends;
   the first end comprising an orifice that can occupy either a first or a second position, wherein said first position is flat and generally closed, and said second position is generally circular and open;
   the second end comprising at least two flexible members, each of the flexible members including an edge region having no frame structure, and
   wherein a length of said orifice between at least two opposing free edges of the first end when said orifice is generally closed is equal to about 1.5 to 2 times the diameter of a patient's right ventricular outflow tract or blood vessel.

2. The vascular valve of claim 1, wherein the valve is attachable to walls of a patient's blood vessel by at least one of suturing, and implantation of prongs attached to the flexible members into the wall of the right ventricular outflow tract or blood vessel.

3. The vascular valve of claim 1 wherein the tubular element is formed of either one of a fluoropolymer, polytetrafluoroethylene, and a biocompatible, synthetic resin.

4. The vascular valve of claim 1, further including an outer tubular structure, the flexible members attached to the outer tubular structure such that said tubular element is disposed within the outer tubular structure.

5. The vascular valve of claim 4, wherein the outer tubular structure includes either a stent, a graft tube, or both a stent and a graft tube.

6. The vascular valve of claim 1, wherein said generally tubular element is formed from a sheet of flexible material having a generally elliptical shape with a minor axis.

7. The vascular valve of claim 6, wherein said flexible material is a synthetic biocompatible material.

8. The vascular valve of claim 6, wherein said flexible material comprises one of a fluoropolymer, polytetrafluoroethylene, and a biocompatible, synthetic resin.

9. The vascular valve of claim 6, wherein said orifice is an incision in said elliptical shape along said minor axis, and said two flexible members are formed from folding said elliptical shape along said minor axis.

10. The vascular valve of claim 9, wherein said incision has ends that are each about a 1 mm to 3 mm distance from an edge of the elliptical shape.

11. The vascular valve of claim 10, wherein said ends are each about 2 mm from said edge of said elliptical shape.

* * * * *